(12) United States Patent
Draget et al.

(10) Patent No.: US 10,966,926 B2
(45) Date of Patent: Apr. 6, 2021

(54) ORAL PHARMACEUTICAL DISPERSION COMPOSITIONS

(75) Inventors: Kurt Ingar Draget, Tromso (NO); Steinar Johan Engelsen, Tromos (NO); Tore Seternes, Tromso (NO); Magnus Hattrem, Tromso (NO); Ingvild Johanne Haug, Tromso (NO)

(73) Assignee: VITUX GROUP AS, Oslo (NO)

( * ) Notice: Subject to any disclaimer, the term of this patent is extended or adjusted under 35 U.S.C. 154(b) by 248 days.

(21) Appl. No.: 14/111,442

(22) PCT Filed: Oct. 19, 2011

(86) PCT No.: PCT/GB2011/052027
§ 371 (c)(1),
(2), (4) Date: Jan. 17, 2014

(87) PCT Pub. No.: WO2012/140392
PCT Pub. Date: Oct. 18, 2012

(65) Prior Publication Data
US 2014/0163108 A1    Jun. 12, 2014

(30) Foreign Application Priority Data
Apr. 11, 2011 (WO) ............... PCT/GB2011/000563

(51) Int. Cl.
| | |
|---|---|
| *A61K 31/192* | (2006.01) |
| *A61K 9/10* | (2006.01) |
| *A61K 9/06* | (2006.01) |
| *A61K 9/107* | (2006.01) |
| *A61K 31/165* | (2006.01) |
| *A61K 31/4045* | (2006.01) |
| *A61K 31/42* | (2006.01) |
| *A61K 31/485* | (2006.01) |
| *A61K 31/4985* | (2006.01) |
| *A61K 31/5415* | (2006.01) |

(52) U.S. Cl.
CPC ............... *A61K 9/10* (2013.01); *A61K 9/06* (2013.01); *A61K 9/107* (2013.01); *A61K 31/165* (2013.01); *A61K 31/192* (2013.01); *A61K 31/4045* (2013.01); *A61K 31/42* (2013.01); *A61K 31/485* (2013.01); *A61K 31/4985* (2013.01); *A61K 31/5415* (2013.01); *Y02A 50/30* (2018.01)

(58) Field of Classification Search
CPC .................................................... A61K 31/192
USPC ........................................................ 514/570
See application file for complete search history.

(56) References Cited

U.S. PATENT DOCUMENTS

| | | | |
|---|---|---|---|
| 3,137,630 A | 6/1964 | Hecker et al. | |
| 4,975,465 A | 12/1990 | Motola | |
| 5,928,664 A * | 7/1999 | Yang | A23G 3/346 424/440 |
| 5,932,245 A * | 8/1999 | Wunderlich et al. | 424/451 |
| 6,066,332 A | 5/2000 | Wunderlich et al. | |
| 6,432,442 B1 | 8/2002 | Buehler et al. | |
| 6,482,465 B1 | 11/2002 | Cherukuri et al. | |
| 2002/0035161 A1 | 3/2002 | Segura et al. | |
| 2003/0193102 A1 | 10/2003 | Yan | |
| 2005/0019416 A1 | 1/2005 | Yan | |
| 2006/0165795 A1 | 7/2006 | Sawicka | |
| 2007/0026075 A1 | 2/2007 | Shudo et al. | |
| 2008/0031928 A1 * | 2/2008 | Steele | A23G 3/36 424/440 |
| 2008/0193520 A1 | 8/2008 | Moschwitzer | |
| 2009/0221563 A1 | 9/2009 | Biesmans | |
| 2010/0209524 A1 | 8/2010 | Yan | |
| 2011/0268771 A1 | 11/2011 | Seternes et al. | |
| 2012/0045486 A1 | 2/2012 | Bravo Cordero et al. | |
| 2013/0005740 A1 * | 1/2013 | Lowther | A23G 3/0004 514/255.04 |
| 2014/0005179 A1 | 1/2014 | Draget | |

FOREIGN PATENT DOCUMENTS

| | | |
|---|---|---|
| CA | 2002472 | 5/2000 |
| CN | 1234230 A | 11/1999 |
| CN | 101045041 A | 10/2007 |
| CN | 101579311 A | 11/2009 |
| EP | 0390369 A2 | 10/1990 |
| EP | 0950402 A2 | 10/1999 |
| EP | 1020193 | 7/2000 |
| EP | 2380657 A1 | 10/2011 |
| JP | 2-178224 | 7/1990 |
| JP | 2-286615 | 11/1990 |

(Continued)

OTHER PUBLICATIONS

"Emulsion", IUPAC, Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org.*
Japanese Patent Office, "Notification of Reasons for Rejection", Dispatched Jul. 14, 2015, in Corresponding Japanese Patent Application No. 2014-504385.
European Patent Office, "Examination Report", dated Feb. 11, 2015 in corresponding Application No. 11 781 582.9.
Courts, A., "The N-Terminal Amino Acid Residues of Gelatin. 2. Thermal Degradation" The British Gelatins and Glue Research Association 58:74-79 (1954).

(Continued)

Primary Examiner — Raymond J Henley, III
(74) Attorney, Agent, or Firm — IpHorgan Ltd.

(57) ABSTRACT

The invention provides an oral pharmaceutical composition, optionally in dose unit form, comprising a lipophilic drug substance in dispersion in a physiologically tolerable aqueous carrier, preferably an aqueous gel, wherein said drug substance contains a functional electrostatic group having a pKa value of from 2 to 10, characterised in that said aqueous carrier has a pH at least 0.3 below or above said pKa value, said pH being below said pKa where said group is acidic and above said pKa where said group is basic.

5 Claims, 2 Drawing Sheets

(56) References Cited

FOREIGN PATENT DOCUMENTS

| | | | | |
|---|---|---|---|---|
| JP | 11-130658 | 5/1999 | | |
| JP | 11-269099 | 10/1999 | | |
| JP | 2000-157212 | 6/2000 | | |
| JP | 2001-508061 | 6/2001 | | |
| JP | 2005-187416 | 7/2005 | | |
| JP | 2005-529128 | 9/2005 | | |
| JP | 2006-504620 | 2/2006 | | |
| JP | 2006-514688 | 5/2006 | | |
| JP | 2007-525413 | 9/2007 | | |
| JP | 2008-523024 | 7/2008 | | |
| JP | 2008-538552 | 10/2008 | | |
| JP | 2009-67790 | 4/2009 | | |
| JP | 2009-526760 | 7/2009 | | |
| WO | 98/30207 | 7/1998 | | |
| WO | 99/16470 | 4/1999 | | |
| WO | 02069936 A3 | 2/2003 | | |
| WO | 03077842 | 9/2003 | | |
| WO | 03/090726 | 11/2003 | | |
| WO | 2004054539 A1 | 7/2004 | | |
| WO | 2004/066925 | 8/2004 | | |
| WO | 2005/000265 | 1/2005 | | |
| WO | 2006/100281 | 9/2006 | | |
| WO | 2007085835 | 1/2007 | | |
| WO | 2007085840 | 8/2007 | | |
| WO | 2010041015 A2 | 4/2010 | | |
| WO | 2010041017 A2 | 4/2010 | | |
| WO | 2010058853 A1 | 5/2010 | | |
| WO | 2010122357 A2 | 10/2010 | | |
| WO | WO-2011014960 A1 * | 2/2011 | .......... | A23G 3/0004 |
| WO | 2011128634 A2 | 10/2011 | | |

OTHER PUBLICATIONS

Eurasian Patent Office, "Conclusion on Patentability" (including English language translation), dated Nov. 18, 2014 in corresponding Application No. 201391369/28.

Shokhin et al., "Comparative dissolution kinetics of generic ibuprofen". Vestnik VGU, edition: Chemistry. Biology. Pharmacy. No. 2 (2009) (including partial English language summary in #3 above).

Chinese Patent Office, "The Notification of the First Office Action", dated Nov. 26, 2014 (including English language translation) in corresponding Application No. 201180070775.0.

European Patent Office, "Bibliographic data: CN1234230A", Espacenet (1999).

Search Report by the UK Intellectual Property Office, UK patent application No. 1006218.0.

International Search Report and Written Opinion of the International Searching Authority, European Patent Office acting as International Searching Authority, International patent application No. PCT/GB2011/000563, dated May 7, 2012.

International Search Report and Written Opinion of the International Searching Authority, European Patent Office acting as International Searching Authority, International patent application No. PCT/GB2011/052027, dated Mar. 21, 2012.

Written Opinion of the International Preliminary Examining Authority, European Patent Office acting as International Preliminary Examining Authority, International patent application No. PCT/GB2011/052027, dated May 3, 2013.

International Preliminary Report on Patentability, European Patent Office acting as International Preliminary Examining Authority, International patent application No. PCT/GB2011/052027, dated Jul. 30, 2013.

Surh, J et al, "Properties and Stability of Oil-in-Water Emulsions Stabilized by Fish Gelatin", Food Hydrocolloids, Elsevier BV, NL, vol. 20, No. 5, Jul. 1, 2006, pp. 596-606.

Office Action by the United States Patent and Trademark Office. U.S. Appl. No. 13/641,088, dated May 22, 2014.

Office Action by the European Patent Office. Application No. 11 715 603.4-1455, dated Sep. 11, 2013.

Office Action by the Eurasian Patent Office. Application No. 201290983/28, dated Sep. 24, 2014.

Japanese Patent Office, Office Action issued in counterpart Japanese Application No. 2016/177656 dated Jun. 20, 2017, with English language translation.

Machine translation of JP 2000-157212 into the English language, created Jun. 20, 2017.

"logP and logD Calculation." Available from: <http://web.archive.org/web/20080414201256/http://www.chemaxon.com.marvin/help/calculations/logPlogD.html> (Apr. 2008).

XuMuK.ru chemical encyclopedia. <http://www.xumuk.ru/encyklopedia/958.html> (2014).

The Cambridge Advanced Learner's Dictionary & Thesaurus. Definition of "gel" <http://dictionary.cambridge.org/ru/%D1%81%D0%BB%D0%BE%D0%B0%D1%8C/%D0%B1%D1%80%D0%B8%D1%82%D0%B0%D0%BD%D1%81%D0%BA%D0%B8%D0%B9/gel> (2014).

Japanese Patent Office, "Notification of Reasons for Rejection" dispatched May 10, 2018 in Japanese Application No. 2016-177656 (both original document and English language translation provided).

Luger et al., "Structure and physicochemical properties of meloxicam, a new NSAID" Eur. J. Pharm Sci. 4(3):175-187 (1996).

Machine translation of JP 2009-67790 into English language.

Machine translation of JP 11-130658 into English language.

European Patent Office, Examination report pursuant to Article 94(3) EPC, dated Jan. 31, 2020 in corresponding European Patent Application No. 16205962.0.

Shokhin et al., "Comparative dissolution kinetics of generic ibuprofen" Vestnik VGU, edition: Chemistry. Biology. Pharmacy, 2009, No. 2.

Eurasian Patent Office, "Conclusion on Patentability", application No. 201691483/28, dated Feb. 26, 2020.

China National Intellectual Property Administration, Notification of the First Office Action, dated Apr. 9, 2020 in corresponding Chinese Patent Application No. 2017111831708.

Industrial Pharmacy, China Medical Science and Technology Press, Second Edition, pp. 325, Jun. 2010.

Medicinal Chemistry, Huazhong University of Science and Technology Press, pp. 54, Jan. 2010.

Molecular Pharmacy, Hunan Normal University Press, pp. 137, Jan. 2010.

* cited by examiner

ORAL PHARMACEUTICAL DISPERSION COMPOSITIONS

This invention relates to oral pharmaceutical compositions in the form of dispersions, preferably gelled aqueous emulsions, particularly gelled oil-in-water emulsions, preferably comprising a hydrophilic drug substance, but optionally a lipophilic or amphiphilic drug substance and to methods of treatment of a human subject therewith.

Many drug substances, i.e. the physiologically active components of pharmaceutical compositions, have an unpleasant taste and/or odour. Accordingly, any therapeutic or prophylactic dosage regime which involves the consumption of unpleasant tasting or nasty smelling dose units is inherently at risk of patient non-compliance.

Moreover, when the unit dose of a drug substance is large, the oral unit dosage forms, e.g. tablets or capsules, may likewise be large and so difficult for elderly or young patients to swallow and moreover may cause a gagging reaction even with healthy adults. Accordingly, any therapeutic or prophylactic dosage regime which involves the consumption of large numbers of dose units or numbers of large, difficult to swallow, dose units is inherently at risk of patient non-compliance.

For some drug substances it is possible to use a chewable tablet, a suckable lozenge, or a film that dissolves in the mouth as the vehicle for the drug substance. Nevertheless, this is not feasible where the drug substance has a bitter or unpleasant taste or where it is primarily intended to be taken up lower down the gastrointestinal tract.

We have previously found that drug substances may be administered without these problems when contained within a piece of soft, chewable, gelled oil-in-water emulsion. Lipophilic drugs may be dissolved in the lipid phase. Where the drug substance is a hydrophilic drug, this may be dissolved in an aqueous phase within said oil-in-water emulsion, i.e. as a gelled water-in-oil-in water emulsion (a "double emulsion").

We have now surprisingly found that, rather than, or in addition to, dissolving the drug in the innermost phase of the emulsion (i.e. the lipophilic drug in the oil phase of an oil-in-water emulsion or the hydrophilic drug in the aqueous phase of a water-in-oil-in water emulsion) the drug substance may be dispersed as a solid, e.g. in particulate form, in whatever phase is most convenient. In this way a particularly high drug loading of the emulsion may be achieved thus reducing the need for the patient to consume multiple or oversized dosage units. Particularly preferably, the invention comprises dispersion of a hydrophilic drug in the lipid phase of a gelled oil-in-water emulsion, and more particularly a lipophilic drug dispersed in the continuous aqueous phase of a gelled oil-in-water emulsion.

This is especially useful when the drug substances to be administrated have a strong, unpleasant taste.

Thus viewed from one aspect the invention provides an oral pharmaceutical composition comprising a drug substance contained in a physiologically tolerable gelled oil-in-water emulsion, wherein said drug substance is a hydrophilic drug dispersed in the lipid phase or a lipophilic drug substance dispersed in a, preferably continuous, aqueous phase of the emulsion.

The gelled emulsions of the invention are preferably in soft, chewable form.

Hydrophilic drugs, i.e. those which may be dispersed in, but not fully dissolved in, the lipid phase include those characterised by their physicochemical properties in that they carry electrostatic charges (e.g. salts) and/or a substantial amount of polar functions such as hydroxyl, keto, phosphate, amino and/or sulphydryl groups. Examples of particular hydrophilic drug substances for use according to the invention include: pyroxidine, sulfamethoxazole, guanethidine monosulphate, leocovorin, lithium salt, naproxen sodium, bismuth subsalicylate, sodium acetazolamide, acetyl salicylic acid, aminophylline, amiodarone hydrochloride, ascorbic acid, atenolol, bendroflumethiazide, calcium folinate, captopril, cetrizine hydrochloride, chloramphenicol sodium succinate, chlorpheniramine maleate, chlorpromazine hydrochloride, cimetidine hydrochloride, ciprofloxacin hydrochloride, clindamycin hydrochloride, clonidine hydrochloride, codeine phosphate, cyclizine hydrochloride, cyclophosphamide, sodium dexamethasone phosphate, sodium dicloxacillin, dicyclomide hydrochloride, diltiazem hydrochloride, diphenhydramine hydrochloride, disopyramide phosphate, doxepin hydrochloride, enalapril maleate, erythromycin ethylsuccinate, flecanide acetate, fluphenazine hydrochloride, folic acid, granisteron hydrochloride, guaifenesin, haloperidol lactate, hydralazin hydrochloride, hydrochloroquine sulfate, hydromorphone hydrochloride, hydroxyzine hydrochloride, sodium indomethacin, isoniazid, isoprenaline hydrochloride, ketorolac trometamol, labetalol hydrochloride, lisinopril, lithium sulfate, mesoridazine benzylate, methadone hydrochloride, methylphenidate hydrochloride, methylprednisolone sodium succinate, metorprolol tartrate, metronidazole hydrochloride, metyldopa, mexiletine hydrochloride, molidone hydrochloride, morphine sulfate, naltrexone hydrochloride, neomycin sulfate, ondanstreon hydrochloride, orciprenaline sulfate, sodium oxacillin, oxybutynin chloride, oxycodone hydrochloride, paracetamol, penicillamine, pentoxifylline, petidine hydrochloride, sodium phenobarbital, potassium phenoxymethylpenicillin, phenylephrine hydrochloride, sodium phenytoin, potassium iodide, primaquine phosphate, procainamide hydrochloride, procarbazine hydrochloride, prochlorperazine maleate, promazine hydrochloride, promethazine hydrochloride, propranolol hydrochloride, pseudoephedrine hydrochloride, pyridostigmine bromide, pyridoxine hydrochloride, ranitidine hydrochloride, salbutamol sulfate, sodium ethacrynate, sotalol hydrochloride, sumatripan succinate, terbinafine hydrochloride, terbutaline sulfate, tetracycline hydrochloride, thioridazine hydrochloride, thiothixene hydrochloride, trifluoperazine hydrochloride, triprolidine hydrochloride, sodium valproate, vancomycin hydrochloride, vancomycin hydrochloride, verapamil hydrochloride, sodium warfarin.

Suitable doses for selected drugs are: sulfamethoxazole (200 mg), guanethidine monosulphate (10 mg), leucovorin (5 mg), lithium salt (300 mg), naproxen sodium (250 mg), bismuth subsalicylate (250 mg), guaifenesin, (200 mg), ketorolac trometamol (10 mg), cyclophosphamide (25 mg), phenoxymethylpenicillin (125 mg), Metronidazol (250 mg). Further suitable doses are given in the tables below.

In a further aspect the invention involves the dispersion of a lipophilic drug in the aqueous phase of an oil in water emulsion (i.e. the continuous phase) or a water-in-oil-in-water emulsion (i.e. the continuous aqueous phase and/or the discontinuous aqueous phase).

Thus viewed from a further aspect, the present invention provides an oral pharmaceutical composition comprising a drug substance contained in a physiologically tolerable gelled oil-in-water emulsion, wherein said drug substance is a lipophilic drug dispersed in an aqueous phase.

Suitable lipophilic drugs are well documented and include temazepam; diphenhydramine; zolpidem; triazolam; nitrazepam; testosterone; estradiol; progesterone; benzodiazepines; barbiturates; cyclosporine; insulin; calcitonin; dextromethorphan; pseudoephedrine; phenylpropanolamine; bromocryptine; apomorphine; selegiline; amitriptyline; dextroamphetamine; phentermine; mazindol; compazine; chlorpromazine; perphenazine; fluoxetine, buspirone; clemastine; chlorpheniramine; dexochlorpheniramine; astemizole; loratadine; paracetamol; ketoprofen; naproxen; and, particularly, ibuprofen.

The present invention involves the dispersion of a drug in a phase of an emulsion in which it is not fully soluble. The drug substance therefore remains in solid, e.g. crystalline form to some extent in the compositions, methods and uses of the invention.

In addition to a hydrophilic drug being dispersed in a lipid phase and/or a lipophilic drug being dispersed in an aqueous phase in the gelled compositions comprising oil-in-water emulsions of the invention, further drug/phase combinations may be present in the gelled compositions, whether by dispersion and/or dissolution. For example, the following compositions are envisaged:

Hydrophilic drug dispersed in lipid phase and hydrophilic drug dissolved in aqueous phase.
Hydrophilic drug dispersed in lipid phase and lipophilic drug dissolved in lipid phase.
Hydrophilic drug dispersed in lipid phase and lipophilic drug dissolved in lipid phase and hydrophilic drug dissolved in aqueous phase.
Hydrophilic drug dispersed in oil phase and lipophilic drug dispersed in aqueous phase.
Lipophilic drug dispersed in aqueous phase and lipophilic drug dissolved in lipid phase.
Lipophilic drug dispersed in aqueous phase and hydrophilic drug dissolved in aqueous phase.
Lipophilic drug dispersed in aqueous phase and hydrophilic drug dissolved in aqueous phase and lipophilic drug dissolved in lipid phase.

In each case the hydrophilic drugs in the phases may be the same or different and the lipophilic drugs in the phases may be the same or different. Amphiphilic drugs may also be present.

In one aspect of the invention the compositions of the invention comprise a lipophilic drug dispersed in the continuous aqueous phase of an oil in water emulsion in the gelled emulsions of the invention.

In order to facilitate even dispersion throughout the phase containing it, the drug substance is preferably in particulate form. The optimal particle size for good dispersion and good mouthfeel of the resulting gelled emulsion varies depending on the nature of the drug and the composition of the phase in which it is dissolved, however suitable particle sizes (e.g. mode maximum particle dimension) are 0.5-25 μm, preferably 1-20 μm, particularly 2-15 μm.

Particularly preferably the compositions of the invention will contain two or more drugs, or even one or more lipophilic drugs in combination with one or more hydrophilic drugs, where the drugs are dispersed in the aqueous and oil phases of an emulsion respectively.

The compositions of the invention are preferably in dose unit form, and each dose until will typically contain 10% to 100%, preferably 50% to 100% of the recommended daily (or one-off) dose of the particular drug substance. Examples of recommended daily or one-off doses for some of the drug substances mentioned herein are set out in Table 1 below.

Where the human recipient is a child, the compositions according to the invention are especially suitable since they can readily and accurately be divided, for example by cutting with a blade, to provide the dosage required for the child's particular age or bodyweight/size. For this reason it is preferred to mark the dose unit (e.g. with surface markings such as a scale of bodyweight, height or age) or its packaging (e.g. the blister or blister cover of a blister-packed gelled emulsion) with indications showing where the gelled emulsion dose unit may be divided to yield a fragment containing the desired dosage.

TABLE 1

Typical daily or one-off drug doses

| Drug substance | Dose per dose unit (mg) |
|---|---|
| Ibuprofen | 100-1500 (e.g. 200, 400, 600 and 800) |
| Naproxen | 250, 375 and 500 |
| Ketoprofen | 12.5-300 (e.g. 12.5, 50, 75, 100 and 200) |
| Paracetamol | 500-1000 |
| Loratadine | 10 |
| Astemizole | 10, 50 and 200 |
| Dexochlorpheniramine | 2-12 (e.g. 2, 4, 6 and 8) |
| Chlorpheniramine | 4 |
| Clemastine | 1 and 2 (as fumarate, 1.34 and 2.68) |
| Diphenhydramine | 25 and 50 |
| Buspirone | 5, 10, 15, and 30 |
| Fluoxetine | 5-90 (e.g. 10 and 20) |
| Perphenazine | 2, 4, 8 and 16 |
| Chlorpromazine | 10, 25, 50, 100 and 200 |
| Prochlorperazine | 5, 10 and 15 |
| Mazindol | 1, 2 and 3 |
| Phentermine | 8-40 (e.g. 8, 15 and 30) |
| Dextroamphetamine | 5, 10 and 15 |
| Amitriptyline | 10, 25, 50, 75, 100 and 150 |
| Selegiline | 1.25, 5 and 10 |
| Apomorphine | 5 and 10 |
| Bromocryptine | 2.5 to 40 (e.g. 2.5, 5, 10, 15) |
| Phenylpropanolamine | 25, 50, 75, 400 and 600 |
| Pseudoephedrine | 60 and 120 |
| Dextromethorphan | 30-600 (e.g. 30, 90, 400) |
| Calcitonin | 5, 30, 35, 75 and 150 |
| Insulin | Recommended daily dose |
| Cyclosporine | 25 and 100 |
| Barbiturate (butabarbital) | 30, 50 and 100 |
| Benzodiazepine (e.g. temazepam, triazolam and nitrazepam) | 0.25, 0.5, 1 and 2 |
| Progesterone | 100, 200 and 300 |
| Estradiol (as estradiol valerinate) | 0.5, 1 and 2 |
| Testosterone (as testosterone undecanoate) | 10 |
| Nitrazepam | 0.3, 1, 2.5, 5 and 10 |
| Triazolam | 0.125, 0.25 and 0.5 |
| Zolpidem | 5 and 10 |
| Temazepam | 7.5, 15, 22.5 and 30 |
| Ergocalciferol | 10-200 kIU (e.g. 30000 IU) |
| Alphacalcidol | 0.25, 0.5, 1 and 2 micrograms |
| Calcitriol | 0.25, 0.5, 1 and 2 micrograms |

The selegiline, apomorphine, insulin and calcitonin dose units are preferably dissolved in the mouth rather than chewed/swallowed.

TABLE 2

| Drug substance | Dose per dose unit (mg) |
|---|---|
| Acetazolamide sodium | 125 |
| Acetyl salicylic acid | 75 |
| Aminophylline | 100 |
| Amiodarone hydrochloride | 100 |
| Ascorbic acid | 25-100 |
| Atenolol | 25-100 |
| Bendroflumethiazide | 5-10 |
| Calcium folinate | 5-25 |
| Captopril | 12.5-100 |
| Cetrizine hydrochlorid | 2.5-10 |
| Chloramphenicol sodium succinate | 125 |

TABLE 2-continued

| Drug substance | Dose per dose unit (mg) |
| --- | --- |
| Chlorpheniramine maleate | 2-12 |
| Chlorpromazine hydrochloride | 10-100 |
| Cimetidine hydrochloride | 100 |
| Ciprofloxacin hydrochloride | 100 |
| Clindamycin hydrochloride | 75-150 |
| Clonidine hydrochloride | 0.1-0.3 |
| Codeine phosphate | 15-60 |
| Cyclizine hydrochloride | 50-150 |
| Cyclophosphamide | 25-50 |
| Dexamethasone sodium phosphate | 0.25-6 |
| Dicloxacillin sodium | 125 |
| Dicyclomide hydrochloride | 20 |
| Diltiazem hydrochloride | 30-120 |
| Diphenhydramine hydrochloride | 12.5-50 |
| Disopyramide phosphate | 100 |
| Doxepin hydrochloride | 10-150 |
| Enalapril maleate | 2.5 |
| Erythromycin ethylsuccinate | 100 |
| Flecanide acetate | 50-150 |
| Fluphenazine hydrochloride | 1-10 |
| Folic acid | 0.4-1 |
| Granisteron hydrochloride | 1 |
| Guafenesin | 100 |
| Haloperidol lactate | 0.5-20 |
| Hydralazin hydrochloride | 10-100 |
| Hydrochloroquine sulphate | 200 |
| Hydromorphone hydrochloride | 1-8 |
| Hydroxyzine hydrochloride | 10-100 |
| Indomethacin sodium | 25-75 |
| Isoniazid | 50-100 |
| Isoprenaline hydrochloride | 10-15 |
| Ketorolac trometamol | 10 |
| Labetalol hydrochloride | 100 |
| Lisinopril | 2.5-40 |
| Lithium sulphate | 42-83 |
| Mesoridazine bensylate | 10-100 |
| Methadone hydrochloride | 5-40 |
| Methylphenidate hydrochloride | 5-20 |
| Methylprednisolone sodium succinate | 2-32 |
| Metorprolol tartrate | 50-100 |
| Metronidazole hydrochloride | 250 |
| Metyldopa | 125 |
| Mexiletine hydrochloride | 150 |
| Molidone hydrochloride | 5-100 |
| Morphine sulphate | 15-200 |
| Naltrexone hydrochloride | 50 |
| Neomycin sulphate | 125 |
| Ondanstreon hydrochloride | 4-8 |
| Orciprenaline sulphate | 10-20 |
| Oxacillin sodium | 250 |
| Oxybutynin chloride | 5 |
| Oxycodone hydrochloride | 5-80 |
| Paracetamol | 80-160 |
| Penicillamine | 125 |
| Pentoxifylline | 400 |
| Petidine hydrochloride | 50-100 |
| Phenobarbital sodium | 15-100 |
| Phenoxymethylpenicillin potassium | 125 |
| Phenylephrine hydrochloride | 10 |
| Phenytoin sodium | 50-100 |
| Potassium iodide | 130 |
| Primaquine phosphate | 15 |
| Procainamide hydrochloride | 250 |
| Procarbazine hydrochloride | 50 |
| Prochlorperazine maleate | 5-30 |
| Promazine hydrochloride | 25-50 |
| Promethazine hydrochloride | 12.5-50 |
| Propranolol hydrochloride | 10-160 |
| Pseudoephedrine hydrochloride | 30-120 |
| Pyridostigmine bromide | 60-180 |
| Pyridoxine hydrochloride | 10-200 |
| Ranitidine hydrochloride | 75-150 |
| Salbutamol sulphate | 2-8 |
| Sodium ethacrynate | 25-50 |
| Sotalol hydrochloride | 80-160 |
| Sumatripan succinate | 25-50 |
| Terbinafine hydrochloride | 250 |
| Terbutaline sulphate | 2.5-5 |
| Tetracycline hydrochloride | 125 |
| Thioridazine hydrochloride | 10-150 |
| Thiothixene hydrochloride | 1-20 |
| Trifluoperazine hydrochloride | 1-10 |
| Triprolidine hydrochloride | 2.5 |
| Valproate sodium | 125 |
| Vancomycin hydrochloride | 125 |
| Verapamil hydrochloride | 40-120 |
| Warfarin sodium | 1-10 |

By dispersing the drug substance in an emulsion phase, a greater loading of the drug can be obtained than if it had to be dissolved. In particular, the present invention can dramatically increase the loading capacity of hydrophilic drugs and/or lipophilic drugs in gelled oil-in-water emulsion. Moreover, by administering drugs in the gelled emulsions of the invention, the unpleasant taste of many drug substances can be masked, thus improving patient compliance. The gelled emulsion dosage form also protects the gastrointestinal tract from the irritation which may be experienced from administration of certain drugs, e.g. NSAIDs.

By drug substance is meant a substance having a desirable therapeutic or prophylactic effect other than as a nutrient, i.e. substances of the type for which regulatory approval as a drug is required in for example the US or the European Union. Less preferably, the drug substance may be a vitamin which classifies as a drug substance for regulatory purposes, e.g. vitamin A, K or D (e.g. ergocalciferol, alphacalcidol and calcitriol). Vitamins, including these, as well as mineral and/or herbs may of course be included in the compositions in addition to non-vitamin drug substances.

By amphiphilic drug substance is meant a drug substance that will distribute at the oil droplet surface. In the single emulsion of the present invention the amphiphilic drug substance is mixed with the oil phase and in the double emulsion of the present invention the amphiphilic drug substance is mixed either with the oil or with the discontinuous aqueous phase of the double emulsion.

Examples of categories of suitable drug substances for use according to the invention include: analgesics; anti-inflammatories; anticancer agents; cardiovascular agents; biological agents; antiallergy agents (e.g. antihistamines); decongestants; antinausea agents, drugs affecting gastrointestinal function, drugs acting on the blood and blood-forming organs, drugs affecting renal and cardiovascular function, antifungal agents, urological agents, hormones, antimicrobial agents, antiepileptical agents, psycholeptical agents, antipsychotic agents, psychoanaleptical agents, anticholinesterase agents, drugs acting on the respiration organs and drugs acting on the eye.

Viewed from a further aspect the invention provides a pharmaceutical composition, comprising a drug substance contained in a physiologically tolerable gelled oil-in-water emulsion, wherein said drug substance is a hydrophilic drug dispersed in an oil phase and/or a lipophilic drug dispersed in a, preferably continuous, aqueous phase of the emulsion for use in medicine.

Viewed from a further aspect the invention provides a pharmaceutical composition, comprising a drug substance contained in a physiologically tolerable gelled oil-in-water emulsion, wherein said drug substance is a hydrophilic drug dispersed in an oil phase and/or a lipophilic drug dispersed in a, preferably continuous, aqueous phase of the emulsion for use in the treatment of retroviral infection, tuberculosis, pneumonia, malaria, leprosy, erectile dysfunction, cancer, cardiovascular diseases, hypertension, pain, bacterial infection, vitamin deficiency or inflammation.

Viewed from a still further aspect the invention provides the use of a drug substance for the manufacture of a medicament for use by oral administration in the treatment of retroviral infection, tuberculosis, pneumonia, malaria, leprosy, erectile dysfunction, cancer, cardiovascular diseases, hypertension, pain, bacterial infection, vitamin deficiency or inflammation, wherein said drug substance is contained in a physiologically tolerable gelled oil-in-water emulsion and is a hydrophilic drug dispersed in an oil phase and/or a lipophilic drug dispersed in a, preferably continuous, aqueous phase of the emulsion.

Viewed from a still further aspect the invention provides a method of treatment of a human subject to combat retroviral infection, tuberculosis, pneumonia, malaria, leprosy, erectile dysfunction, cancer, cardiovascular diseases, hypertension, pain, bacterial infection, vitamin deficiency or inflammation, which method comprises orally administering to said subject an effective amount of a pharmaceutical composition comprising a drug substance contained in a physiologically tolerable gelled oil-in-water emulsion, wherein said drug substance is a hydrophilic drug dispersed in an oil phase and/or a lipophilic drug dispersed in a, preferably continuous, aqueous phase of the emulsion.

The drug substance may typically be included in the compositions of the invention at 10% to 100% of its normal oral daily dose, especially 50% to 100%.

Besides the drug substance, the compositions of the invention may contain further components such as nutrients, e.g. lipids, (especially triglycerides and phospholipids, typically of plant or marine animal origin), vitamins, minerals, and folic acid, pH modifiers, viscosity modifiers, flavours, aromas, sweeteners, colorants, antioxidants, etc.

The gelled emulsion compositions of the invention will preferably be in dose unit form, with each dose unit having a weight of 50 to 3000 mg, especially 100 to 2000 mg, particularly 100 to 1500 mg, more particularly 400 to 1500 mg, more especially 400 to 1000 mg.

The composition of the invention will preferably be uncoated, i.e. not within a capsule or shell-coating. Accordingly, to avoid water loss during storage, the dose units will conveniently be individually packaged, e.g. in foil wrappers or in the blisters of a blister pack.

The dose units of the gelled emulsion may be formed for example by moulding, extrusion or cutting or the like. For adult use, the dose units are preferably in tablet or lozenge form; however for child use they may conveniently be presented in child-friendly form, e.g. geometric shapes such as rods, strips and tubes, or animal, doll, or vehicle shapes, for example the shape of a popular cartoon character.

The oil phase of the oil-in-water emulsion may be any physiologically tolerable lipid, e.g. fatty acid esters such as triglycerides and phospholipids, for example plant or animal oils, especially plant and marine animal oils. Particularly preferably an oil is used which is high in omega-3, omega-6 or omega-9 essential fatty acids, especially omega-3 essential fatty acids, more especially EPA and DHA. In this way the oil phase itself is a highly bioavailable source of nutrient lipids.

Examples of omega-3 acids include α-linolenic acid (ALA), stearidonic acid (SDA), eicosatrienoic acid (ETE), eicosatetraenoic acid (ETA), eicosapentaenoic acid (EPA), docosapentaenoic acid (DPA), docosahexaenoic acid (DHA), tetracosapentaenoic acid and tetracosahexaenoic acid. Examples of omega-6 acids include linoleic acid, gamma-linolenic acid, eicosadienoic acid, dihomo-gamma-linolenic acid (DGLA), arachidonic acid (AA), docosadienoic acid, adrenic acid, docosapentaenoic acid, and calendic acid. Examples of omega-9 acids include oleic acid, eicosenoic acid, mead acid, erucic acid and nervonic acid.

It is particularly preferred that the compositions according to the invention contain a citrus flavour (e.g. orange or lemon oil) in order to mask any remaining oil taste on chewing. It is also particularly preferred that the compositions according to the invention contain xylitol, e.g. as 0.5 to 50% wt., preferably 1 to 40% wt., e.g. 15 to 40% wt., in order to mask both taste and mouth feel. These may be in the aqueous phase or the oil phase (e.g. as a water-in-oil-in water emulsion), or both; however inclusion in the aqueous phase will generally be sufficient.

Other than the drug substance, the essential fatty acids may form part or the whole of the oil phase in the gelled emulsion, preferably at least 10% wt, more especially at least 50% wt, particularly at least 80% wt. of that phase. They may be used as single compounds or as compound mixtures, e.g. plant or marine oils.

The oil phase of the oil-in-water emulsion may also contain solubilisers in order to increase the solubility of the drug substance in the oil phase. Suitable solubilisers would be known to a person skilled in the art and include Chremophor EL™, castor oil, Tween 80™, Solutol™ HS15, Lutrol™ and Olestra.

The aqueous phase of the gelled emulsion will contain water and a physiologically tolerable gelling agent, e.g. a hydrocolloid such as gelatin, alginate, carrageenan or a pectin. Such gelling agents and their gel-forming properties are well known. See for example Phillips GO and Williams P A (Eds.) *Handbook of hydrocolloids*, Woodhead Publishing, Cambridge (2000). The use of gelatin is especially preferred.

Besides water and the gelling agent, the aqueous phase of the gelled emulsion may contain other water-soluble components, e.g. vitamins, minerals, pH modifiers, viscosity modifiers, antioxidants, colorants, flavours, water-soluble drug substances, etc. as desired.

The weight ratio of the lipid phase to the aqueous phase in the gelled emulsions is preferably 1:19 to 3:1, especially 35:65 to 1:1, particularly 2:3 to 1:1.

Emulsion formation may be effected by conventional techniques; however emulsification under a non-oxidising gas, e.g. nitrogen, is preferred. Likewise, the components of the emulsion are preferably degassed before emulsification and handling and packaging of the set emulsion is preferably performed under such a gas.

The gelled emulsions of and used according to the invention may be produced as described in WO 2007/085835 and WO 2007/085840 and PCT/GB2009/002404 and PCT/GB2009/002406 the contents of which are hereby incorporated by reference.

The gelled emulsions may if desired be more than biphasic. Thus a water-in-oil emulsion may be emulsified with an aqueous gelling agent phase to produce a water-in-oil-in-water double emulsion, or two oil-in-water emulsions with different oil phases may be combined and intimately mixed before gelling onset.

As is well known, if even a slight fraction of ibuprofen is dissolved in the mouth this results in a profound off-taste and an unbearable astringent sensation. Conventional ibuprofen tablets are therefore coated with a thick sugar coating to avoid the patient experiencing any adverse effects.

We have also found that in the case of lipophilic drug substances carrying a functional electrostatic group having a pKa value of 2 to 10, more especially 4 to 10, particularly 4.5 to 9, the composition may be presented in the form of an aqueous dispersion of the drug substance and having an aqueous phase pH which is at least 0.3, preferably at least 0.5, more preferably at least 1, for example up to 2.5, preferably up to 2, more preferably up to 1.8, below or above the pKa value of the electrostatic group, the pH being below the pKa value where the electrostatic group is acidic (e.g. a carboxyl group) and above the pKa value where the electrostatic group is basic (e.g. an amine group). Where the drug substance contains two or more functional electrostatic groups, the pH is preferably below or above the lowest acid group pKa or above the highest basic group pKa by these values. In this way, not only is it possible to achieve a high loading of the lipophilic drug compound into the oral pharmaceutical composition but also the unpleasant mouthfeel that otherwise arises with aqueous dispersions of such drugs is masked. If desired, a strong flavouring agent may also be included to further mask mouthfeel, e.g. a citrus fruit flavour such as grapefruit for acidic drugs.

Thus viewed from a further aspect the invention provides an oral pharmaceutical composition, optionally in dose unit form, comprising a lipophilic drug substance in dispersion in a physiologically tolerable aqueous carrier, preferably a continuous aqueous gel, i.e. not an oil-in-water emulsion, wherein said drug substance contains a functional electrostatic group having a pKa value of from 2 to 10, preferably 4 to 9, especially 4.5 to 8.5, characterised in that said aqueous carrier has a pH at least 0.3, preferably at least 0.5, more preferably at least 1 below or above said pKa value, said pH being below said pKa where said group is acidic and above said pKa where said group is basic.

pH and pKa values as referred to herein are preferably as measured at ambient temperature, typically and preferably 21° C.

The aqueous dispersions of the invention may be in any suitable form, e.g. gels, suspensions, viscous liquids (e.g. syrups) or simple dispersions.

Preferably however they are aqueous gels. The gelling agents used may be any physiologically tolerable agents, preferably gelling agents as described elsewhere herein.

Besides water and the gelling agent, the aqueous gel may contain other water-soluble components, e.g. vitamins, minerals, pH modifiers, viscosity modifiers, antioxidants, colorants, flavours, water-soluble drug substances, etc. as desired.

We have surprisingly found that compositions of the invention comprising type B gelatins have much faster drug release profiles than corresponding compositions comprising type A gelatins of the same Bloom strength. This effect is particularly noticeable at high Bloom strength, typically Bloom strengths above 200.

By type A gelatin is meant gelatin obtained from acid treated raw material, e.g. pig skin collagen or fish collagen. Gelatin obtained from acid treated warm water fish gelatin is especially preferred.

By type B gelatin is meant gelatin obtained from alkali treated raw material, e.g. collagen found in bovine hides.

Particularly preferably the gelling agent used in the compositions of the invention is a type B gelatin.

The lipophilic drug substance used in the dispersions of the invention may be any lipophilic drug substances having a functional group with a pKa in the appropriate range; preferably however it is an NSAID, particularly ibuprofen.

Where ibuprofen or ketoprofen is used, the pH of the aqueous carrier is preferably about 4-4.5 as the pKa of the said group in ibuprofen is about 5. Using an aqueous carrier with a pH of 4-4.5 allows the extremely astringent mouthfeel of ibuprofen to be masked and reduces the solubility of ibuprofen in the aqueous carrier.

The desired pH of the aqueous carrier may be achieved by the use of well known physiologically tolerable acids, bases and buffers, e.g. using fruit acids such as citric acid.

As noted above for gelled emulsions, the dispersion compositions of the invention will preferably be in dose unit form, with each dose unit having a weight of 50 to 3000 mg, especially 100 to 2000 mg, particularly 100 to 1500 mg, more particularly 400 to 1500 mg, more especially 400 to 1000 mg. The dose units of the dispersions may be formed for example by moulding, extrusion or cutting or the like. For adult use, the dose units are preferably in tablet or lozenge form; however for child use they may conveniently be presented in child-friendly form, e.g. geometric shapes such as rods, strips and tubes, or animal, doll, or vehicle shapes, for example the shape of a popular cartoon character.

Viewed from a further aspect the invention provides a lipophilic drug substance having a functional electrostatic group having a pKa of 2 to 10 for use in a method of treatment of a human or non human animal (especially a mammal) subject to combat a condition responsive thereto, which method comprises orally administering to said subject an oral pharmaceutical composition comprising said drug substance dispersed in an aqueous carrier having a pH at least 0.3, preferably at least 0.5, more preferably at least 1 below or above said pKa value, said pH being below said pKa where said group is acidic and above said pKa where said group is basic.

Viewed from a further aspect the invention provides the use of a lipophilic drug substance having a functional electrostatic group having a pKa of 2 to 10 for the manufacture of an oral pharmaceutical composition for use by oral administration in a method of treatment of a human or nonhuman animal subject to combat a condition responsive to said drug substance, said composition comprising said drug substance in dispersion in a physiologically tolerable aqueous carrier, preferably an aqueous gel, characterised in that said aqueous carrier has a pH at least 0.3, preferably at least 0.5, more preferably at least 1 below or above said pKa value, said pH being below said pKa where said group is acidic and above said pKa where said group is basic.

Viewed from a still further aspect the invention provides a method of treatment of a human or nonhuman animal subject by oral administration thereto of an effective amount of an oral pharmaceutical composition comprising a lipophilic drug substance having a functional electrostatic group having a pKa of 2 to 10 to combat a condition responsive to said drug substance, said composition comprising said drug substance in dispersion in a physiologically tolerable aqueous carrier, preferably an aqueous gel, characterised in that said aqueous carrier has a pH at least 0.3, preferably at least 0.5, more preferably at least 1 below or above said pKa value, said pH being below said pKa where said group is acidic and above said pKa where said group is basic.

The invention will now be illustrated further with reference to the following non-limiting Examples and the accompanying drawings, in which.

EXAMPLE 1

Drug-Free Composition

Figure 1:
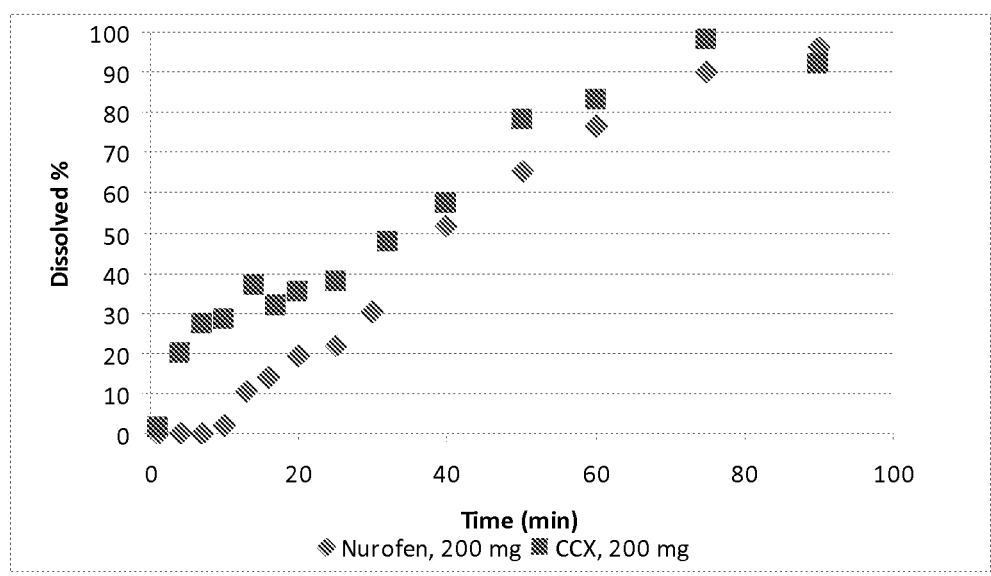
FIG. 1 shows the release profile of ibuprofen from the aqueous compositions of the invention compared to the release profile of standard Nurofen™ tablets (Reckitt Benkieser).

An aqueous phase is formed from the following ingredients:

| | |
|---|---|
| Gelatin | 7.5% wt |
| Xylitol | 36% wt |
| Sorbitol | 14% wt |
| 50% Citric acid | 1% wt |
| Lemon flavour | 0.15% wt |
| Water | ad 100% wt |

Sunflower oil (or alternatively an omega-3 ester (Omacor®)) is emulsified with the aqueous phase in a weight ratio of 45:55 and the emulsion is poured in aliquots of 1.5 g into elongate moulds lined with a metal/plastics laminate blister tray and allowed to set. The blister tray is thermally sealed with a metal/plastics foil cover sheet.

EXAMPLE 2

Drug-Containing Compositions

The drugs listed in Table 1 above are dissolved in the aqueous phase and dispersed in the oil phase used in Example 1 at the concentrations per dose unit set out in Table 1 before emulsions are produced, poured and allowed to set as in Example 1. The set-gel dosage units are packaged as in Example 1.

For drug concentrations below 100 mg per dose unit, the dose units are conveniently 250, 500 or 750 mg. For concentrations above 100 mg per dose unit, the dose units are conveniently 500, 1000, 1500, 2000, 2500 or 3000 mg.

EXAMPLE 3

Components

| | |
|---|---|
| Gelatin | 84 mg |
| Gum arabicum | 55.5 mg |
| Sorbitol | 155 mg |
| Xylitol | 360 mg |
| Citric acid | 9 mg |
| Flavour | 18 mg |
| Colour | 10.5 mg |
| oil | 0-600 mg |
| Sulfamethoxazole | 200 mg |
| Trimethoprim | 40 mg |
| Water | to 1500 mg |

The oil(s) and sulfamethoxazole and trimethoprim are emulsified with the aqueous phase and the emulsion is poured in aliquots of 1.5 g into elongate moulds lined with a metal/plastics laminate blister tray and allowed to set. The blister tray is thermally sealed with a metal/plastics foil cover sheet.

EXAMPLE 4

Components

| | |
|---|---|
| Gelatin | 84 mg |
| Gum arabicum | 55.5 mg |
| Sorbitol | 155 mg |
| Xylitol | 360 mg |
| Citric acid | 9 mg |
| Flavour | 18 mg |
| Colour | 10.5 mg |
| Oil | 0-600 mg |
| Naltrexone | 50 mg |
| Water | to 1500 mg |

The oil(s) and naltrexone are emulsified with the aqueous phase and the emulsion is poured in aliquots of 1.5 g into elongate moulds lined with a metal/plastics laminate blister tray and allowed to set. The blister tray is thermally sealed with a metal/plastics foil cover sheet.

EXAMPLE 5

Components

| | |
|---|---|
| Gelatin | 84 mg |
| Gum arabicum | 55.5 mg |
| Sorbitol | 155 mg |
| Xylitol | 360 mg |
| Citric acid | 9 mg |
| Flavour | 18 mg |
| Colour | 10.5 mg |
| Oil | 0-600 mg |
| Promethazine | 12.5 mg |
| Water | to 1500 mg |

The oil(s) and promethazine are emulsified with the aqueous phase and the emulsion is poured in aliquots of 1.5 g into elongate moulds lined with a metal/plastics laminate blister tray and allowed to set. The blister tray is thermally sealed with a metal/plastics foil cover sheet.

EXAMPLE 6

Components

| | |
|---|---|
| Gelatin | 84 mg |
| Gum arabicum | 55.5 mg |
| Sorbitol | 155 mg |
| Xylitol | 360 mg |
| Citric acid | 9 mg |
| Flavour | 18 mg |
| Colour | 10.5 mg |
| Oil | 0-600 mg |
| leucovorin | 10 mg |
| Water | to 1500 mg |

The oil(s) and leucovorin are emulsified with the aqueous phase and the emulsion is poured in aliquots of 1.5 g into elongate moulds lined with a metal/plastics laminate blister tray and allowed to set. The blister tray is thermally sealed with a metal/plastics foil cover sheet.

EXAMPLE 7

Components

| | |
|---|---|
| Gelatin | 84 mg |
| Gum arabicum | 55.5 mg |

-continued

| | |
|---|---|
| Sorbitol | 155 mg |
| Xylitol | 360 mg |
| Citric acid | 9 mg |
| Flavour | 18 mg |
| Colour | 10.5 mg |
| Oil | 0-600 mg |
| Atenolol | 50 mg |
| Water | to 1500 mg |

The oil(s) and atenolol are emulsified with the aqueous phase and the emulsion is poured in aliquots of 1.5 g into elongate moulds lined with a metal/plastics laminate blister tray and allowed to set. The blister tray is thermally sealed with a metal/plastics foil cover sheet.

EXAMPLE 8

Components

| | |
|---|---|
| Gelatin | 84 mg |
| Gum arabicum | 55.5 mg |
| Sorbitol | 155 mg |
| Xylitol | 360 mg |
| Citric acid | 9 mg |
| Flavour | 18 mg |
| Colour | 10.5 mg |
| Oil | 0-600 mg |
| Sumatriptan | 25 mg |
| Water | to 1500 mg |

The oil(s) and sumatriptan are emulsified with the aqueous phase and the emulsion is poured in aliquots of 1.5 g into elongate moulds lined with a metal/plastics laminate blister tray and allowed to set. The blister tray is thermally sealed with a metal/plastics foil cover sheet.

EXAMPLE 9

Gelled Ibuprofen Dispersions

Crystalline ibuprofen is dispersed at 10% wt concentration in an aqueous solution comprising the ingredients listed below and the dispersion is poured into elongate molds as described in the previous example, allowed to set and sealed.
Contents:

| Ingredient | Content (% wt) |
|---|---|
| Water | 27.45 |
| Gelatin | 11.49 |
| Sorbitol | 18.50 |
| Xylitol | 30.85 |
| Sodium saccharin | 0.0158 |
| Sodium cyclamate | 0.1573 |
| Citric acid | 0.53 |
| Ibuprofen 90 | 10.00 |
| Total | 100.00 |

EXAMPLE 10

Gelled Ibuprofen Dispersions

Crystalline ibuprofen was dispersed at 6.7% wt concentration in an aqueous solution comprising the ingredients listed below and the dispersion was poured into rounded molds as described in the previous examples, allowed to set and sealed.
Contents:

| Ingredient | Content (% wt) |
|---|---|
| Water | 28.46 |
| Gelatin (Type B, 226 Bloom, DGF Stoess) | 11.92 |
| Sorbitol | 19.18 |
| Xylitol | 31.99 |
| Sucralose | 0.310 |
| Orange flavour | 0.900 |
| Citric acid | 0.544 |
| Ibuprofen (Grade 90, BASF) | 6.70 |
| Total | 100.00 |
| Total | 100.00 |

EXAMPLE 11

Comparison of Ibuprofen Release Profiles

Gelled dispersions according to Example 9 (but set in rounded rather than elongate molds) were compared for their ibuprofen release profiles with Nurofen™ tablets (Reckitt Benkieser), i.e. ibuprofen-containing test units having a conventional sugar coating covering the drug and carrier. Both the dispersions and tablets contained 200 mg ibuprofen.

The dispersions and test units were exposed to simulated intestinal juice (Phosphate buffered saline, pH 7.2, Sigma) at 37° C. and with 75 rpm stirring (according to the European Pharmacopoeia) in order to study the release of ibuprofen. The release profiles are shown in FIG. 1 (the square symbols represent the data points for the dispersions and the diamond symbols represent the data points for the Nurofen™ tablets). This Figure surprisingly shows that the gelled dispersions according to Example 9 result in 100% of the ibuprofen being released within 75 minutes, i.e. 10-15 minutes faster than the Nurofen™ tablets.

EXAMPLE 12

Gelled Paracetamol Dispersions

Paracetamol was dispersed at 7.5% wt concentration in an aqueous solution comprising the ingredients listed below and the dispersion was poured into rounded molds as described in the previous examples, allowed to set and sealed.
Contents:

| Ingredient | Content (% wt) |
|---|---|
| Water | 30.09 |
| Gelatin (Type B, 226 Bloom, DGF Stoess) | 18.86 |
| Sorbitol | 12.77 |
| Xylitol | 29.82 |
| Sucralose | 0.135 |
| Peppermint | 0.475 |
| Citric acid | 0.338 |
| Paracetamol (acetaminophen, Sigma) | 7.50 |
| Total | 100.0 |

EXAMPLE 13

Paracetamol Release Profile

Gelled dispersions according to Example 12 were tested for their paracetamol release profiles.

Figure 2:
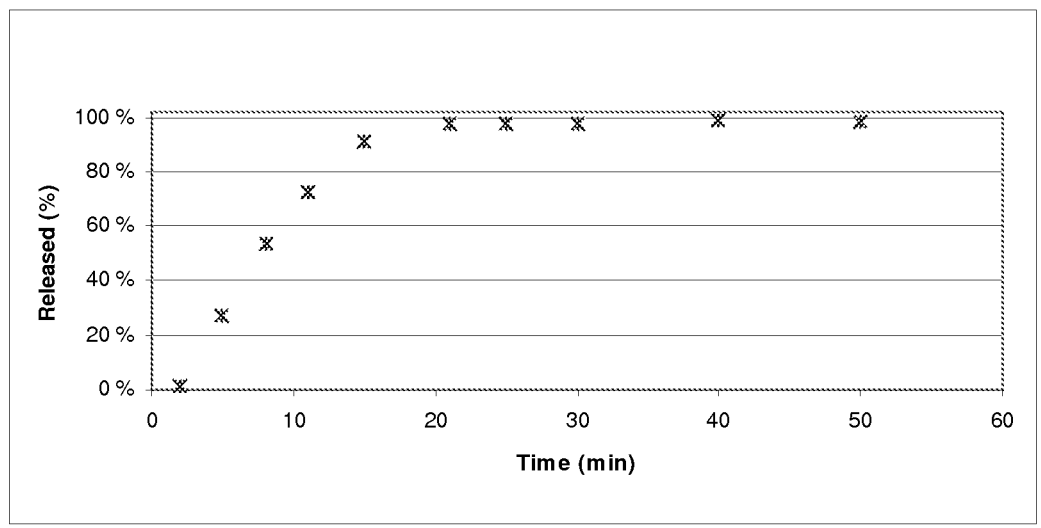
FIG. 2 shows the release profile of paracetamol from the aqueous compositions of the invention.

The dispersions were exposed to simulated gastric juice (0.1 M HCl) at 37° C. and with 75 rpm stirring (according to the European Pharmacopoeia) in order to study the release of paracetamol. The release profile is shown in FIG. 2. It is clear from this Figure that the total release of the paracetamol (100% release) occurs within 20 minutes.

EXAMPLE 14

Gelled Ketoprofen Dispersions

Ketoprofen is dispersed at 2.5% wt concentration in an aqueous solution comprising the ingredients listed below and the dispersion is poured into elongate molds as described in the previous example, allowed to set and sealed.
Contents:

| Ingredient | Content (% wt) |
|---|---|
| Water | 29.95 |
| Gelatin | 12.52 |
| Sorbitol | 20.14 |
| Xylitol | 33.60 |
| Sodium saccharin | 0.0172 |
| Sodium cyclamate | 0.1713 |
| Citric acid | 0.5794 |
| Apple flavour | 0.5667 |
| Ketoprofen | 2.50 |
| Total | 100.0 |

EXAMPLE 15

Gelled Paracetamol and Diphenylhydramine Dispersions

Paracetamol and diphenylhydramine HCl are dispersed in an aqueous solution comprising the ingredients listed below at 7.5 and 0.38% wt concentration, respectively and the dispersion is poured into elongate molds as described in the previous example, allowed to set and sealed.
Contents:

| Ingredient | Content (% wt) |
|---|---|
| Water | 30.09 |
| Gelatin | 18.86 |
| Sorbitol | 12.77 |
| Xylitol | 29.45 |
| Sucralose | 0.135 |
| Citric acid | 0.338 |
| Peppermint | 0.475 |
| Paracetamol | 7.50 |
| Diphenylhydramine HCl | 0.38 |
| Total | 100.0 |

EXAMPLE 16

Gelled Paracetamol, Dextrometorphan and Phenylephrine Dispersions

Paracetamol, dextrometorphan HBr and phenylephrine HCl are dispersed in an aqueous solution comprising the ingredients listed below at 7.5, 0.23 and 0.12% wt concentration, respectively and the dispersion is poured into elongate molds as described in the previous example, allowed to set and sealed.
Contents:

| Ingredient | Content (% wt) |
|---|---|
| Water | 30.09 |
| Gelatin | 18.86 |
| Sorbitol | 12.77 |
| Xylitol | 29.47 |
| Sucralose | 0.135 |
| Citric acid | 0.338 |
| Peppermint | 0.475 |
| Paracetamol | 7.50 |
| Dextrometorphan HBr | 0.23 |
| Phenylephrine HCl | 0.12 |
| Total | 100.0 |

EXAMPLE 17

Gelled Paracetamol, Chlorpheniramine Maleate and Phenylephrine Dispersions

Paracetamol, chlorpheniramine maleate and phenylephrine HCl are dispersed in an aqueous solution comprising the ingredients listed below at 7.5, 0.046 and 0.12% wt concentration, respectively and the dispersion is poured into elongate molds as described in the previous example, allowed to set and sealed.
Contents:

| Ingredient | Content (% wt) |
|---|---|
| Water | 30.09 |
| Gelatin | 18.86 |
| Sorbitol | 12.77 |
| Xylitol | 29.65 |
| Sucralose | 0.135 |
| Citric acid | 0.338 |
| Peppermint | 0.475 |
| Paracetamol | 7.50 |
| Chlorpheniramine maleate | 0.46 |
| Phenylephrine HCl | 0.12 |
| Total | 100.0 |

The invention claimed is:

1. An oral pharmaceutical composition which is set and in uncoated dose unit form, wherein said composition is a physiologically tolerable continuous aqueous gel which is not an oil-in-water emulsion, said continuous aqueous gel comprising water, gelatin as a gelling agent, and a pH modifier, and having dispersed therein uncoated crystalline ibuprofen, and said continuous aqueous gel having a pH in the range of 4 to 4.5.

2. The composition as claimed in claim 1 wherein the gelatin in the physiologically tolerable continuous aqueous gel comprises a type B gelatin.

3. The composition as claimed in claim 1 wherein the gelatin in the physiologically tolerable continuous aqueous gel comprises a type A gelatin.

4. The composition as claimed in claim 2 wherein the gelatin in the physiologically tolerable continuous aqueous gel further comprises a type A gelatin.

5. A method of treatment of a human or non-human animal subject comprising the step of orally administering an effective amount of an oral pharmaceutical composition according to claim 1.

\* \* \* \* \*